(12) United States Patent
Oskam

(10) Patent No.: US 6,593,438 B2
(45) Date of Patent: Jul. 15, 2003

(54) CATALYST COMPOSITION AND METHOD OF POLYMERIZATION

(75) Inventor: John H. Oskam, Flemington, NJ (US)

(73) Assignee: Univation Technologies, LLC, Houston, TX (US)

( * ) Notice: Subject to any disclaimer, the term of this patent is extended or adjusted under 35 U.S.C. 154(b) by 198 days.

(21) Appl. No.: 09/729,551

(22) Filed: Dec. 4, 2000

(65) Prior Publication Data

US 2002/0103071 A1 Aug. 1, 2002

(51) Int. Cl.$^7$ ................................................. C08F 4/06
(52) U.S. Cl. ..................... 526/172; 526/126; 526/130; 526/131; 526/134; 526/147; 526/161; 526/348.3; 526/348.4; 526/348.5; 526/348.6; 526/351; 526/352; 526/308
(58) Field of Search ......................................... 526/172

(56) References Cited

U.S. PATENT DOCUMENTS

| | | | | |
|---|---|---|---|---|
| 5,231,151 A | * | 7/1993 | Spencer et al. | 526/116 |
| 5,599,761 A | * | 2/1997 | Turner et al. | 502/152 |
| 6,218,330 B1 | * | 4/2001 | Razavi et al. | 502/107 |
| 2002/0103071 A1 | * | 8/2002 | Oskam | 502/103 |

OTHER PUBLICATIONS

Renner, P.; Galka, C.; Memmler, H.; Kauper, U.; Gade, L. H. J.Organomet. Chem. 1999, 591, 71–77.*
Mehrkhodavandi, P; Bonitatebus, P. J.; Schrock, R.R. J. Am. Chem. Soc., 2000, 122, 7841.*
Kang, K.K.; Hong, S. .; Jeong, Y.–T.; Shiono, T.; Ikeda, T. J. Polym. Sci. A.; Polym. Chem. 1999, 37(20), 3756 [abstract only].*
Jia, L.; Ding, E.; Rheingold, A. L.; Rhatigan, B. Organometallics 2000, 19, 963.*
Mehrkhodavandi, Parisa et al., "A Comparison of Cationic Zirconium Methyl and IsobutylInitiators that Contain an Arylated Diamido–Pyridine Ligand for Polymerization of 1–Hexene. Elucidation of a Dramatic "Initiator Effect""J. Am. Chem. Soc. 2000, 122, No. 32, 7841–7842.

Blake, Alexander J. Et al., "Highly Selective Trimerization of MeNC by a NovelTitanium Imido Complex Containing a Tridentate Dianionic Ligand", Chem. Commun. (Cambridge), No. 16, 1997, 1555–1556.

Bashall, Alan et al., "C–H bond activation and C–N coupling reactions of methylacetylenes and allenes with an imidotitanium complex", Chem. Commun. (Cambridge), No. 23, 1998 2555–2556.

Friedrich, Stefan et al., "Titanium and Zirconium Complexes Containing a Novel Dianionic Trifunctional Amido Ligand", Chem. Ber./Recl., vol. 130, No. 12, 1997, 1751–1759.

Blake, Alexander J. et al., "Group 4 Imido Complexes Stabilized by a Tridentate Diamido–Donor Ligand", Inorg. Chem. 2001, 40, No. 5, 870–877.

Mehrkhodavandi, Parisa et al., "Cationic Hafnium Alkyl Complexes That are Stable Toward. β–Hydride Elmination below 10° C. and Active as Initiators for the Living Polymerization of 1–Hexene " J. Am. Chem. Soc. 2001, 123, 10746–10747.

Pugh, Stephen M. et al., "Gropu 5 Imido Complexes Supported by Diamido–pyridine Ligands: Aryloxide, Amide, Benzamidinate, Alkyl, and Cyclopentadienyl Derivatives " Organometallics, Vol. 20, No. 16, 2001, 3581–3542.

Pugh, Stephen M. et al., "Group 5 Imido Complexes Derived from Diamido–Pyridine Ligands ", Inorg. Chem., 2001, Vol. 40, No. 16, 3992–4001.

* cited by examiner

Primary Examiner—David W. Wu
Assistant Examiner—Rip A. Lee
(74) Attorney, Agent, or Firm—Jaimes Sher; Kevin M. Faulkner

(57) ABSTRACT

This invention relates to a composition of matter comprising the catalyst compound comprising a transition metal complexed with a facially coordinating tridentate bisamide ligand. The invention is also directed to a catalyst system or a supported catalyst system comprising this compound and an activator and to a process for using the catalyst system or supported catalyst system in a process for polymerizing olefin(s).

17 Claims, No Drawings

CATALYST COMPOSITION AND METHOD OF POLYMERIZATION

FIELD OF THE INVENTION

This invention relates to a catalyst system comprising a catalyst compound and an activator used in an olefin polymerization process, preferably in the gas or slurry phase to produce polyolefins. The catalyst system preferably includes an activator, and a catalyst compound comprising a transition metal complexed with a facially coordinating tridentate bisamide ligand.

BACKGROUND OF THE INVENTION

Advances in polymerization and catalysis have resulted in the capability to produce many new polymers having improved physical and chemical properties useful in a wide variety of superior products and applications. With the development of new catalysts the choice of polymerization (solution, slurry, high pressure or gas phase) for producing a particular polymer has been greatly expanded. Also, advances in polymerization technology have provided more efficient, highly productive and economically enhanced processes. Especially illustrative of these advances is the development of technology utilizing bulky ligand metallocene catalyst systems. In a slurry or gas phase process typically a supported catalyst system is used, however, more recently unsupported catalyst systems are being used in these processes. For example, U.S. Pat. Nos. 5,317,036 and 5,693,727 and European publication EP-A-0 593 083 and PCT publication WO 97/46599 all describe various processes and techniques for introducing liquid catalysts to a reactor. There is a desire in the industry using this technology to reduce the complexity of the process, to improve the process operability, to increase product characteristics and to vary catalyst choices. Thus, it would be advantageous to have a process that is capable of improving one or more of these industry needs.

EP 0 893 454 A1 discloses bisamide based catalyst compounds that can be used for ethylene polymerization. WO 98/45039 discloses polymerization catalysts containing electron withdrawing amide ligands combined with group 3–10 or lanthanide metal compounds used with co-catalysts to polymerize olefins.

SUMMARY OF THE INVENTION

This invention relates to a catalyst system and polymerization processes using that catalyst system.

In one aspect, the invention relates to a catalyst system comprising one or more activators and at least one catalyst compound. The catalyst compound preferably comprises a group 3, 4, 5 lanthanide, or actinide metal atom bound to at least one anionic leaving group and also bound to at least three group 15 atoms, at least one of which is also bound to a group 15 or 16 atom through another group which may be a $C_1$ to $C_{20}$ hydrocarbon group, a heteroatom containing group, silicon, germanium, tin, or phosphorus, wherein the group 15 or 16 atom may also be bound to nothing or a hydrogen, a group 14 atom containing group, a halogen, or a heteroatom containing group, and wherein each of the two group 15 atoms are also bound to a cyclic group and may optionally be bound to hydrogen, a halogen, a heteroatom or a hydrocarbyl group, or a heteroatom containing group.

In a preferred embodiment, the catalyst compound is represented by the formula:

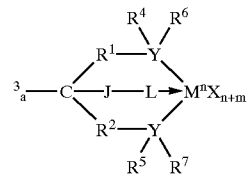

wherein

M is a group 3, 4 or 5 transition metal or a lanthanide or actinide group metal, each X is independently an anionic leaving group, n is the oxidation state of M, a is 0 or 1, m is the formal charge of the YZL ligand, Y is a group 15 element, Z is a group 15 element, J is a $C_1$ to $C_{20}$ hydrocarbon group, a heteroatom containing group, silicon, germanium, tin, or phosphorus, L is a group comprising a group 15 or 16 element, $R^1$ and $R^2$ are independently a $C_1$ to $C_{20}$ hydrocarbon group, a heteroatom containing group, silicon, germanium, tin, or phosphorus, $R^1$ and $R^2$ may also be interconnected to each other, $R^3$ is hydrogen, a hydrocarbyl group or a heteroatom containing group, $R^4$ and $R^5$ are independently an aryl group, a substituted aryl group, a cyclic alkyl group, a substituted cyclic alkyl group, or multiple ring system, and $R^6$ and $R^7$ are independently absent or hydrogen, halogen, heteroatom or a hydrocarbyl group, or a heteroatom containing group.

By "formal charge of the YZL ligand" is meant the charge of the entire ligand absent the metal and the leaving groups X.

By "$R^1$ and $R^2$ may also be interconnected to each other" is meant that $R^1$ and $R^2$ may be bound to each other through other groups.

The activator is preferably an alumoxane, a modified alumoxane, a non-coordinating anion, a borane, a borate, a combination thereof or a conventional-type cocatalyst as described below. It appears preferably however, to use the alumoxanes and boranes together as the inventors have observed that alumoxanes alone and boranes alone do not appear activate the catalysts compounds nearly as well.

BRIEF DESCRIPTION OF THE DRAWINGS

DETAILED DESCRIPTION OF THE INVENTION

In a preferred embodiment, one or more activators are combined with a catalyst compound represented by the formula:

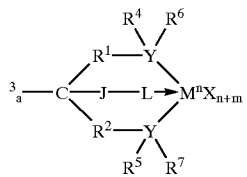

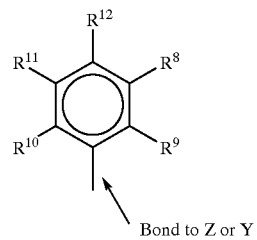

M is a group 3, 4, or 5 transition metal or a lanthanide or actinide group metal, preferably a group 4, preferably zirconium or hafnium, each X is independently an anionic leaving group, preferably hydrogen, a hydrocarbyl group, a heteroatom or a halogen, n is the oxidation state of M, preferably +3, +4, or +5, preferably +4, m is the formal charge of the YZL ligand, preferably 0, −1, −2 or −3, preferably −2, L is a group 15 or 16 element, preferably nitrogen;

J is a $C_1$ to $C_{20}$ hydrocarbon group, a heteroatom containing group having up to twenty carbon atoms, preferably a $C_1$ to $C_6$ hydrocarbon group, preferably a $C_1$ to $C_{20}$ alkyl, aryl or aralkyl group, preferably a linear, branched or cyclic $C_1$ to $C_{20}$ alkyl or group, wherein the alkyl aryl or aralkyl group may be substituted or un-substituted and may contain heteroatoms, and J may form a ring structure with L;

Y is a group 15 element, preferably nitrogen or phosphorus,

Z is a group 15 element, preferably nitrogen or phosphorus, $R^1$ and $R^2$ are independently a $C_1$ to $C_{20}$ hydrocarbon group, a heteroatom containing group having up to twenty carbon atoms, silicon, germanium, tin, or phosphorus, preferably a $C_1$ to $C_6$ hydrocarbon group, preferably a $C_1$ to $C_{20}$ alkyl, aryl or aralkyl group, preferably a linear, branched or cyclic $C_1$ to $C_{20}$ alkyl group, $R^1$ and $R^2$ may also be interconnected to each other, $R^3$ is a hydrocarbon group, hydrogen, a halogen, a heteroatom containing group, preferably a linear, cyclic or branched alkyl group having 1 to 20 carbon atoms;

a is 1;

$R^4$ and $R^5$ are independently an aryl group, a substituted aryl group, a cyclic alkyl group, a substituted cyclic alkyl group, a cyclic aralkyl group, a substituted cyclic aralkyl group or multiple ring system, preferably having up to 20 carbon atoms, preferably between 3 and 10 carbon atoms, preferably a $C_1$ to $C_{20}$ hydrocarbon group, a $C_1$ to $C_{20}$ aryl group or a $C_1$ to $C_{20}$ aralkyl group, and $R^6$ and $R^7$ are independently absent, or hydrogen, halogen, heteroatom or a hydrocarbyl group, preferably a linear, cyclic or branched alkyl group having 1 to 20 carbon atoms, more preferably absent.

An aralkyl group is defined to be a substituted aryl group.

In a preferred embodiment, $R^4$ and $R^5$ are independently a group represented by the following formula:

wherein $R^8$ to $R^{12}$ are each independently hydrogen, a $C_1$ to $C_{40}$ alkyl group, a heteroatom, a heteroatom containing group containing up to 40 carbon atoms, preferably a $C_1$ to $C_{20}$ linear or branched alkyl group, preferably a methyl, ethyl, propyl or butyl group, any two R groups may form a cyclic group and/or a heterocyclic group. The cyclic groups may be aromatic. In a preferred embodiment, $R^9$ and $R^{10}$ are independently a methyl, ethyl, propyl or butyl group, in a preferred embodiment, $R^9$ and $R^{10}$ are methyl groups, and $R^8$, $R^{11}$ and $R^{12}$ are hydrogen. In this embodiment, M is preferably zirconium or hafnium, most preferably zirconium; each of L, Y, and Z is nitrogen; each of $R^1$ and $R^2$ is —$CH_2$—; $R^3$ is methyl; and $R^6$ and $R^7$ are absent.

The catalyst compounds described herein are preferably combined with one or more activators to form an olefin polymerization catalyst system. Preferred activators include alumoxanes, modified alumoxanes, non-coordinating anions, non-coordinating group 13 metal or metalliod anions, boranes, borates and the like. It is within the scope of this invention to use alumoxane or modified alumoxane as an activator, and/or to also use ionizing activators, neutral or ionic, such as tri (n-butyl) ammonium tetrakis (pentafluorophenyl) boron or a trisperfluorophenyl boron metalloid precursor which ionize the neutral metallocene compound. Other useful compounds include triphenyl boron, triethyl boron, tri-n-butyl ammonium tetraethylborate, triaryl borane and the like. Other useful compounds include aluminate salts as well.

In a preferred embodiment, MMAO3A (modified methyl alumoxane in heptane, commercially available from Akzo Chemicals, Inc. under the trade name Modified Methylalumoxane type 3A, (See U.S. Pat. No. 5,041,584) is combined with the metal compounds to form a catalyst system.

There are a variety of methods for preparing alumoxane and modified alumoxanes, non-limiting examples of which are described in U.S. Pat. Nos. 4,665,208, 4,952,540, 5,091, 352, 5,206,199, 5,204,419, 4,874,734, 4,924,018, 4,908,463, 4,968,827, 5,308,815, 5,329,032, 5,248,801, 5,235,081, 5,157,137, 5,103,031, 5,391,793, 5,391,529, 5,041,584 5,693,838, 5,731,253, 5,041,584 and 5,731,451 and European publications EP-A-0 561 476, EP-B1-0 279 586 and EP-A-0 594-218, and PCT publication WO 94/10180, all of which are herein fully incorporated by reference.

Ionizing compounds may contain an active proton, or some other cation associated with but not coordinated to or only loosely coordinated to the remaining ion of the ionizing compound. Such compounds and the like are described in European publications EP-A-0 570 982, EP-A-0 520 732, EP-A-0 495 375, EP-A-0 426 637, EP-A-500 944, EP-A-0 277 003 and EP-A-0 277 004, and U.S. Pat. Nos. 5,153,157, 5,198,401, 5,066,741, 5,206,197, 5,241,025, 5,387,568, 5,384,299, 5,502,124 and 5,643,847, all of which are herein fully incorporated by reference. Other activators include those described in PCT publication WO 98/07515 such as tris (2,2',2"- nonafluorobiphenyl) fluoroaluminate, which is fully incorporated herein by reference. Combinations of activators are also contemplated by the invention, for example, alumoxanes and ionizing activators in combinations, see for example, PCT publications WO 94/07928 and WO 95/14044 and U.S. Pat. Nos. 5,153,157 and 5,453,410 all of which are herein fully incorporated by reference. Also, methods of activation such as using radiation and the like are also contemplated as activators for the purposes of this invention.

Useful activators include those selected from the group consisting of:

trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethyl-(2,4,6-trimethylanilinium) tetraphenylborate, trimethylammonium tetrakis(pentafluorophenyl)borate, triethylammonium tetrakis(pentafluorophenyl)borate, tripropylammonium tetrakis(pentafluorophenyl)borate, tri(n-butyl)ammonium tetrakis(pentafluorophenyl) borate, tri(sec-butyl)ammonium tetrakis (pentafluorophenyl)borate, N,N-dimethylanilinium tetrakis(pentafluorophenyl)borate, N,N-diethylanilinium tetrakis(pentafluorophenyl)borate, N,N-dimethyl-(2,4,6-trimethylanilinium) tetrakis (pentafluorophenyl)borate, trimethylammonium tetrakis-(2,3,4,6-tetrafluorophenylborate, triethylammonium tetrakis-(2,3,4,6-tetrafluorophenyl)borate, tripropylammonium tetrakis-(2,3,4,6-tetrafluorophenyl)borate, tri(n-butyl)ammonium tetrakis-(2,3,4,6-tetrafluoro-phenyl)borate, dimethyl(t-butyl)ammonium tetrakis-(2,3,4,6-tetrafluorophenyl) borate, N,N-dimethylanilinium tetrakis-(2,3,4,6-tetrafluorophenyl)borate, N,N-diethylanilinium tetrakis-(2,3,4,6-tetrafluoro-phenyl)borate, N,N-dimethyl-(2,4,6-trimethylanilinium)tetrakis-(2,3,4,6-tetrafluorophenyl)borate; di-(i-propyl)ammonium tetrakis(pentafluorophenyl)borate, dicyclohexylammonium tetrakis(pentafluorophenyl)borate; triphenylphosphonium tetrakis(pentafluorophenyl)borate, tri(o-tolyl) phosphonium tetrakis(pentafluorophenyl)borate, tri(2, 6-dimethylphenyl)phosphonium tetrakis (pentafluorophenyl)borate, and mixtures thereof.

In another embodiment, a second catalyst compound may be present. The second catalyst compound mat be another compound as described above or may comprise a conventional-type transition metal catalyst.

Conventional-Type Transition Metal Catalysts

Conventional-type transition metal catalysts are those traditional Ziegler-Natta, vanadium and Phillips-type catalysts well known in the art. Such as, for example Ziegler-Natta catalysts as described in "Ziegler-Natta Catalysts and Polymerizations", John Boor, Academic Press, New York, 1979. Examples of conventional-type transition metal catalysts are also discussed in U.S. Pat. Nos. 4,115,639, 4,077, 904, 4,482,687, 4,564,605, 4,721,763, 4,879,359 and 4,960, 741 all of which are herein fully incorporated by reference. The conventional-type transition metal catalyst compounds that may be used in the present invention include transition metal compounds from Groups 3 to 17, preferably 4 to 12, more preferably 4 to 6 of the Periodic Table of Elements.

These conventional-type transition metal catalysts may be represented by the formula: $MR_x$, where M is a metal from Groups 3 to 17, preferably Group 4 to 6, more preferably Group 4, most preferably titanium; R is a halogen or a hydrocarbyloxy group; and x is the oxidation state of the metal M. Non-limiting examples of R include alkoxy, phenoxy, bromide, chloride and fluoride. Non-limiting examples of conventional-type transition metal catalysts where M is titanium include $TiCl_4$, $TiBr_4$, $Ti(OC_2H_5)_3Cl$, $Ti(OC_2H_5)Cl_3$, $Ti(OC_4H_9)_3Cl$, $Ti(OC_3H_7)_2Cl_2$, $Ti(OC_2H_5)_2Br_2$, $TiCl_3.1/3AlCl_3$ and $Ti(OC_{12}H_{25})Cl_3$.

Conventional-type transition metal catalyst compounds based on magnesium/titanium electron-donor complexes that are useful in the invention are described in, for example, U.S. Pat. Nos. 4,302,565 and 4,302,566, which are herein fully incorporate by reference. The $MgTiCl_6$ (ethyl acetate)$_4$ derivative is particularly preferred.

British Patent Application 2,105,355 and U.S. Pat. No. 5,317,036, herein incorporated by reference, describes various conventional-type vanadium catalyst compounds. Non-limiting examples of conventional-type vanadium catalyst compounds include vanadyl trihalide, alkoxy halides and alkoxides such as $VOCl_3$, $VOCl_2(OBu)$ where Bu=butyl and $VO(OC_2H_5)_3$; vanadium tetra-halide and vanadium alkoxy halides such as $VCl_4$ and $VCl_3(OBu)$; vanadium and vanadyl acetyl acetonates and chloroacetyl acetonates such as $V(AcAc)_3$ and $VOCl_2(AcAc)$ where (AcAc) is an acetyl acetonate. The preferred conventional-type vanadium catalyst compounds are $VOCl_3$, $VCl_4$ and $VOCl_2$-OR where R is a hydrocarbon radical, preferably a $C_1$ to $C_{10}$ aliphatic or aromatic hydrocarbon radical such as ethyl, phenyl, isopropyl, butyl, propyl, n-butyl, iso-butyl, tertiary-butyl, hexyl, cyclohexyl, naphthyl, etc., and vanadium acetyl acetonates.

Conventional-type chromium catalyst compounds, often referred to as Phillips-type catalysts, suitable for use in the present invention include $CrO_3$, chromocene, silyl chromate, chromyl chloride ($CrO_2Cl_2$), chromium-2-ethyl-hexanoate, chromium acetylacetonate ($Cr(AcAc)_3$), and the like. Non-limiting examples are disclosed in U.S. Pat. Nos. 3,709,853, 3,709,954, 3,231,550, 3,242,099 and 4,077,904, which are herein fully incorporated by reference.

Still other conventional-type transition metal catalyst compounds and catalyst systems suitable for use in the present invention are disclosed in U.S. Pat. Nos. 4,124,532, 4,302,565, 4,302,566, 4,376,062, 4,379,758, 5,066,737, 5,763,723, 5,849,655, 5,852,144, 5,854,164 and 5,869,585 and published EP-A2 0 416 815 A2 and EP-A1 0 420 436, which are all herein incorporated by reference.

Other catalysts may include cationic catalysts such as $AlCl_3$, and other cobalt, iron, nickel and palladium catalysts well known in the art. See for example U.S. Pat. Nos. 3,487,112, 4,472,559, 4,182,814 and 4,689,437 all of which are incorporated herein by reference.

Typically, these conventional-type transition metal catalyst compounds excluding some conventional-type chromium catalyst compounds are activated with one or more of the conventional-type cocatalysts described below.

Conventional-Type Cocatalysts

Conventional-type cocatalyst compounds for the above conventional-type transition metal catalyst compounds may be represented by the formula $M^3M^4{}_vX^2{}_cR^3{}_{b-c}$, wherein $M^3$ is a metal from Group 1 to 3 and 12 to 13 of the Periodic Table of Elements; $M^4$ is a metal of Group 1 of the Periodic Table of Elements; v is a number from 0 to 1; each $X^2$ is any halogen; c is a number from 0 to 3; each $R^3$ is a monovalent hydrocarbon radical or hydrogen; b is a number from 1 to 4; and wherein b minus c is at least 1. Other conventional-type organometallic cocatalyst compounds for the above conventional-type transition metal catalysts have the formula $M^3R^3_k$, where $M^3$ is a Group IA, IIA, IIB or IIIA metal, such as lithium, sodium, beryllium, barium, boron, aluminum, zinc, cadmium, and gallium; k equals 1, 2 or 3 depending upon the valency of $M^3$ which valency in turn normally depends upon the particular Group to which $M^3$ belongs; and each $R^3$ may be any monovalent hydrocarbon radical.

Non-limiting examples of conventional-type organometallic cocatalyst compounds useful with the conventional-type catalyst compounds described above include methyllithium, butyllithium, dihexylmercury, butylmagnesium, diethylcadmium, benzylpotassium, diethylzinc, tri-n-butylaluminum, diisobutyl ethylboron, diethylcadmium, di-n-butylzinc and tri-n-amylboron, and, in particular, the aluminum alkyls, such as tri-hexyl-aluminum, triethylaluminum, trimethylaluminum, and tri-isobutylaluminum. Other conventional-type cocatalyst compounds include mono-organohalides and hydrides of Group 2 metals, and mono- or di-organohalides and hydrides of Group 3 and 13 metals. Non-limiting examples of such conventional-type cocatalyst compounds include di-isobutylaluminum bromide, isobutylboron dichloride, methyl magnesium chloride, ethylberyllium chloride, ethylcalcium bromide, di-isobutylaluminum hydride, methylcadmium hydride, diethylboron hydride, hexylberyllium hydride, dipropylboron hydride, octylmagnesium hydride, butylzinc hydride, dichloroboron hydride, di-bromo-aluminum hydride and bromocadmium hydride. Conventional-type organometallic cocatalyst compounds are known to those in the art and a more complete discussion of these compounds may be found in U.S. Pat. Nos. 3,221,002 and 5,093,415, which are herein fully incorporated by reference.

The second catalyst compound may also be compound referred to as a metallocene, i.e. those mono-and bis-cyclopentadienyl group 4, 5 and 6 compounds described in U.S. Pat. Nos. 4,530,914, 4,805,561, 4,871,705, 4,937,299, 5,096,867, 5,120,867, 5,210,352, 5,124,418, 5,017,714, 5,057,475, 5,064,802, 5,278,264, 5,278,119, 5,304,614, 5,324,800, 5,347,025, 5,350,723, 5,391,790, 5,391,789, 5,399,636, 5,539,124, 5,455,366, 5,534,473, 5,684,098, 5,693,730, 5,698,634, 5,710,297, 5,712,354, 5,714,427, 5,714,555, 5,728,641, 5,728,839, EP-A-0 591 756, EP-A-0 520 732, EP-A-0 578,838, EP-A-0 638,595, EP-A-0 420 436, EP-B1-0 485 822, EP-B1-0 485 823, EP-A-0 743 324, EP-B1-0 518 092, WO 91/04257, WO 92/00333, WO 93/08221, WO 93/08199, WO 94/01471, WO 94/07928, WO 94/03506 WO 96/20233, WO 96/00244, WO 97/15582, WO 97/15602, WO 97/19959, WO 97/46567, WO 98/01455, WO 98/06759 and WO 95/07140, all of which are fully incorporated by reference herein.

Supports, Carriers and General Supporting Techniques

The catalyst and/or the activator may be placed on, deposited on, contacted with, incorporated within, adsorbed, or absorbed in a support. Typically the support can be of any of the solid, porous supports, including microporous supports. Typical support materials include talc; inorganic oxides such as silica, magnesium chloride, alumina, silica-alumina; polymeric supports such as polyethylene, polypropylene, polystyrene, cross-linked polystyrene; and the like. Preferably the support is used in finely divided form. Prior to use the support is preferably partially or completely dehydrated. The dehydration may be done physically by calcining or by chemically converting all or part of the active hydroxyls. For more information on how to support catalysts please see U.S. Pat. No. 4,808,561 which discloses how to support a metallocene catalyst system. The techniques used therein are generally applicable for this invention.

For example, in a most preferred embodiment, the activator is contacted with a support to form a supported activator wherein the activator is deposited on, contacted with, vaporized with, bonded to, or incorporated within, adsorbed or absorbed in, or on, a support or carrier.

Support materials of the invention include inorganic or organic support materials, preferably a porous support material. Non-limiting examples of inorganic support materials include inorganic oxides and inorganic chlorides. Other carriers include resinous support materials such as polystyrene, functionalized or crosslinked organic supports, such as polystyrene divinyl benzene, polyolefins or polymeric compounds, or any other organic or inorganic support material and the like, or mixtures thereof.

The preferred support materials are inorganic oxides that include those Group 2, 3, 4, 5, 13 or 14 metal oxides. The preferred supports include silica, fumed silica, alumina (WO 99/60033), silica-alumina and mixtures thereof. Other useful supports include magnesia, titania, zirconia, magnesium chloride (U.S. Pat. No. 5,965,477), montmorillonite (EP-B1 0 511 665), phyllosilicate, zeolites, talc, clays (U.S. Pat. No. 6,034,187) and the like. Also, combinations of these support materials may be used, for example, silica-chromium, silica-alumina, silica-titania and the like. Additional support materials may include those porous acrylic polymers described in EP 0 767 184 B1, which is incorporated herein by reference. Other support materials include nanocomposites as described in PCT WO 99/47598, aerogels as described in WO 99/48605, spherulites as described in U.S. Pat. No. 5,972,510 and polymeric beads as described in WO 99/50311, which are all herein incorporated by reference. A preferred support is fumed silica available under the trade name Cabosil™ TS-610, available from Cabot Corporation. Fumed silica is typically a silica with particles 7 to 30 nanometers in size that has been treated with dimethylsilyldichloride such that a majority of hydroxyl groups are capped.

It is preferred that the support material, most preferably an inorganic oxide, has a surface area in the range of from about 10 to about 700 $m^2/g$, pore volume in the range of from about 0.1 to about 4.0 cc/g and average particle size in the range of from about 5 to about 500 μm. More preferably, the surface area of the support is in the range of from about 50 to about 500 $m^2/g$, pore volume of from about 0.5 to about 3.5 cc/g and average particle size of from about 10 to about 200 μm. Most preferably the surface area of the support is in the range from about 100 to about 1000 $m^2/g$, pore volume from about 0.8 to about 5.0 cc/g and average particle size is from about 5 to about 100 μm. The average pore size of the support material of the invention typically has pore size in the range of from 10 to 1000 Å, preferably 50 to about 500 Å, and most preferably 75 to about 450 Å.

There are various methods known in the art for producing a supported activator or combining an activator with a support material. In an embodiment, the support material is chemically treated and/or dehydrated prior to combining with the catalyst compound, activator and/or catalyst system.

In one embodiment, an alumoxane is contacted with a support material, preferably a porous support material, more preferably a inorganic oxide, and most preferably the support material is silica.

In an embodiment, the support material having a various levels of dehydration, preferably 200° C. to 600° C. dehydrated silica, that is then contacted with an organoaluminum or alumoxane compound. In specifically the embodiment wherein an organoaluminum compound is used, the activator is formed in situ in or on the support material as a result of the reaction of, for example, trimethylaluminum and water.

In yet another embodiment, a Lewis base-containing support substrates will react with a Lewis acidic activator to form a support bonded Lewis acid compound. The Lewis base hydroxyl groups of silica are exemplary of metal/metalloid oxides where this method of bonding to a support occurs. This embodiment is described in U.S. patent application Ser. No. 09/191,922, filed Nov. 13, 1998, which is herein incorporated by reference. Other embodiments of supporting an activator are described in U.S. Pat. No. 5,427,991, where supported non-coordinating anions derived from trisperfluorophenyl boron are described; U.S. Pat. No. 5,643,847 discusses the reaction of Group 13 Lewis acid compounds with metal oxides such as silica and illustrates the reaction of trisperfluorophenyl boron with silanol groups (the hydroxyl groups of silicon) resulting in bound anions capable of protonating transition metal organometallic catalyst compounds to form catalytically active cations counter-balanced by the bound anions; immobilized Group IIIA Lewis acid catalysts suitable for carbocationic polymerizations are described in U.S. Pat. No. 5,288,677; and James C. W. Chien, Jour. Poly. Sci.: Pt A: Poly. Chem, Vol. 29, 1603–1607 (1991), describes the olefin polymerization utility of methylalumoxane (MAO) reacted with silica ($SiO_2$) and metallocenes and describes a covalent bonding of the aluminum atom to the silica through an oxygen atom in the surface hydroxyl groups of the silica.

In an embodiment, the weight percent of the activator to the support material is in the range of from about 10 weight percent to about 70 weight percent, preferably in the range of from 20 weight percent to about 60 weight percent, more preferably in the range of from about 30 weight percent to about 50 weight percent, and most preferably in the range of from 30 weight percent to about 40 weight percent.

In another embodiment, the catalyst compounds and/or the activators are preferably combined with a support material such as a particulate filler material and then spray dried, preferably to form a free flowing powder. Spray drying may be by any means known in the art. Please see EP A 0 668 295 B1, U.S. Pat. No. 5,674,795 and U.S. Pat. No. 5,672,669 which particularly describe spray drying of supported catalysts. In general one may spray dry the catalysts by placing the catalyst compound and the optional activator in solution (allowing the catalyst compound and activator to react, if desired), adding a filler material such as silica or fumed silica, such as Gasil™ or Cabosil™, then forcing the solution at high pressures through a nozzle. The solution may be sprayed onto a surface or sprayed such that the droplets dry in midair. The method generally employed is to disperse the silica in toluene, stir in the activator solution, and then stir in the catalyst compound solution. Typical slurry concentrations are about 5–8 wt %. This formulation may sit as a slurry for as long as 30 minutes with mild stirring or manual shaking to keep it as a suspension before spray-drying. In one preferred embodiment, the makeup of the dried material is about 40–50 wt % activator (preferably alumoxane), 50–60 $SiO_2$ and about ~2 wt % catalyst compound.

The first and second catalyst compounds may be combined at molar ratios of 1:1000 to 1000:1, preferably 1:99 to 99:1, preferably 10:90 to 90:10, more preferably 20:80 to 80:20, more preferably 30:70 to 70:30, more preferably 40:60 to 60:40. The particular ratio chosen will depend on the end product desired and/or the method of activation. One practical method to determine which ratio is best to obtain the desired polymer is to start with a 1:1 ratio, measure the desired property in the product produced and adjust the ratio accordingly.

The melt index (and other properties) of the polymer produced may be changed by manipulating hydrogen concentration in the polymerization system by:

1) changing the amount of the first catalyst in the polymerization system, and/or
2) changing the amount of the second catalyst, if present, in the polymerization system, and/or
3) adding hydrogen to the polymerization process; and/or
4) changing the amount of liquid and/or gas that is withdrawn and/or purged from the process; and/or
5) changing the amount and/or composition of a recovered liquid and/or recovered gas returned to the polymerization process, said recovered liquid or recovered gas being recovered from polymer discharged from the polymerization process; and/or
6) using a hydrogenation catalyst in the polymerization process; and/or
7) changing the polymerization temperature; and/or
8) changing the ethylene partial pressure in the polymerization process; and/or
9) changing the ethylene to hexene ratio in the polymerization process; and/or
10) changing the activator to transition metal ratio in the activation sequence.

In a preferred embodiment, the hydrogen concentration in the reactor is about 200–2000 ppm, preferably 250–1900 ppm, preferably 300–1800 ppm, preferably 350–1700 ppm, preferably 400–1600 ppm, preferably 500–1500 ppm, preferably 500–1400 ppm, preferably 500–1200 ppm, preferably 600–1200 ppm, preferably 700–1100 ppm, more preferably 800–1000 ppm.

In general the catalyst compound(s) and the activator(s) are combined in ratios of about 1000:1 to about 0.5:1. In a preferred embodiment, the metal compounds and the activator are combined in a ratio of about 300:1 to about 1:1, preferably about 150:1 to about 1:1, for boranes, borates, aluminates, etc. the ratio is preferably about 1:1 to about 10:1 and for alkyl aluminum compounds (such as diethylaluminum chloride combined with water) the ratio is preferably about 0.5:1 to about 10:1.

The catalyst system, the catalyst compounds and or the activator (whether spray dried or not) are preferably introduced into the reactor in one or more solutions or one or more slurries. In one embodiment, a solution of the activated catalyst compound(s) in an alkane such as pentane, hexane, toluene, isopentane or the like is introduced into a gas phase or slurry phase reactor. In another embodiment, a slurry of the activated catalyst compound(s) is introduced into a gas phase or slurry phase reactor. The slurry is preferably a suspension of particulate materials in a diluent medium. Preferably the slurry comprises mineral oil or other hydrocarbon as the diluent, typically an alkane having from 3 to 7 carbon atoms, preferably a branched alkane can be used as the diluent. The medium employed should be liquid under the conditions of polymerization and relatively inert. When a propane medium is used the process must be operated above the reaction diluent critical temperature and pressure. Preferably, a hexane or an isobutane medium is employed.

In another embodiment, a slurry of the catalyst compound (s) in mineral oil or an alkane such as pentane, hexane, toluene, isopentane or the like is combined with a solution of the activator and is introduced into a gas phase or slurry phase reactor. In another embodiment, the catalysts system or the components can be introduced into the reactor in a suspension or an emulsion. In one embodiment, the catalyst compound(s) are contacted with the activator in a solvent and just before the solution is fed into a gas or slurry phase reactor.

Solutions of the catalyst compounds are prepared by taking the catalyst compound and dissolving it in any solvent such as an alkane, toluene, xylene, etc. The solvent may first be purified in order to remove any poisons that may affect the catalyst activity, including any trace water and/or oxygenated compounds. Purification of the solvent may be accomplished by using activated alumina and activated supported copper catalyst, for example. The catalyst is preferably completely dissolved into the solution to form a homogeneous solution. Multiple catalysts may be dissolved into the same solvent, if desired. Once the catalysts are in solution, they may be stored indefinitely until use.

A slurry used in the process of this invention is typically prepared by suspending the activator and/or catalyst compound in a liquid diluent. The liquid diluent is typically an alkane having from 3 to 7 carbon atoms, preferably a branched alkane or an organic composition such as mineral oil The diluent employed should be liquid under the conditions of polymerization and relatively inert. The concentration of the components in the slurry is controlled such that a desired ratio of catalyst compound(s) to activator, and/or catalyst compound to catalyst compound is fed into the reactor. The components are generally fed into the polymerization reactor as a mineral oil slurry. Solids concentrations in oil are about 10 to 15 weight %, preferably 11–14 weight %. In some embodiments, the spray dried particles are <~10 micrometers in size from the lab-scale Buchi spray-dryer, while the scaled up rotary atomizers can create particles ~25 micrometers, compared to conventional supported catalysts which are ~50 micrometers. In a preferred embodiment, the particulate filler has an average particle size of 0.001 to 1 microns, preferably 0.001 to 0.1 microns.

Polymerization Process

The metal compounds and catalyst systems described above are suitable for use in any polymerization process, including solution, gas or slurry processes or a combination thereof, most preferably a gas or slurry phase process.

In one embodiment, this invention is directed toward the polymerization or copolymerization reactions involving the polymerization of one or more monomers having from 2 to 30 carbon atoms, preferably 2–12 carbon atoms, and more preferably 2 to 8 carbon atoms. The invention is particularly well suited to the copolymerization reactions involving the polymerization of one or more olefin monomers of ethylene, propylene, butene-1, pentene-1,4-methyl-pentene-1, hexene-1, octene-1, decene-1,3-methyl-pentene-1,3,5,5-trimethyl-hexene-1 and cyclic olefins or a combination thereof. Other monomers can include vinyl monomers, diolefins such as dienes, polyenes, norbornene, norbornadiene monomers. Preferably a copolymer of ethylene is produced, where the comonomer is at least one alpha-olefin having from 4 to 15 carbon atoms, preferably from 4 to 12 carbon atoms, more preferably from 4 to 8 carbon atoms and most preferably from 4 to 7 carbon atoms.

In another embodiment, ethylene or propylene is polymerized with at least two different comonomers to form a terpolymer. The preferred comonomers are a combination of alpha-olefin monomers having 4 to 10 carbon atoms, more preferably 4 to 8 carbon atoms, optionally with at least one diene monomer. The preferred terpolymers include the combinations such as ethylene/butene-1/hexene-1, ethylene/propylene/butene-1, propylene/ethylene/hexene-1, ethylene/propylene/norbornene and the like.

In a particularly preferred embodiment, the process of the invention relates to the polymerization of ethylene and at least one comonomer having from 4 to 8 carbon atoms, preferably 4 to 7 carbon atoms. Particularly, the comonomers are butene-1,4-methyl-pentene-1, hexene-1 and octene-1, the most preferred being hexene-1 and/or butene-1.

Typically in a gas phase polymerization process a continuous cycle is employed where in one part of the cycle of a reactor system, a cycling gas stream, otherwise known as a recycle stream or fluidizing medium, is heated in the reactor by the heat of polymerization. This heat is removed from the recycle composition in another part of the cycle by a cooling system external to the reactor. Generally, in a gas fluidized bed process for producing polymers, a gaseous stream containing one or more monomers is continuously cycled through a fluidized bed in the presence of a catalyst under reactive conditions. The gaseous stream is withdrawn from the fluidized bed and recycled back into the reactor. Simultaneously, polymer product is withdrawn from the reactor and fresh monomer is added to replace the polymerized monomer. (See for example U.S. Pat. Nos. 4,543,399, 4,588,790, 5,028,670, 5,317,036, 5,352,749, 5,405,922, 5,436,304, 5,453,471, 5,462,999, 5,616,661 and 5,668,228 all of which are fully incorporated herein by reference.)

The reactor pressure in a gas phase process may vary from about 10 psig (69 kPa) to about 500 psig (3448 kPa), preferably in the range of from about 100 psig (690 kPa) to about 400 psig (2759 kPa), preferably in the range of from about 200 psig (1379 kPa) to about 400 psig (2759 kPa), more preferably in the range of from about 250 psig (1724 kPa) to about 350 psig (2414 kPa).

The reactor temperature in the gas phase process may vary from about 30° C. to about 120° C., preferably from about 60° C. to about 115° C., more preferably in the range of from about 75° C. to about 110° C., and most preferably in the range of from about 85° C. to about 110° C. Altering the polymerization temperature can also be used as a tool to alter the final polymer product properties.

The productivity of the catalyst or catalyst system is influenced by the main monomer partial pressure. The preferred mole percent of the main monomer, ethylene or propylene, preferably ethylene, is from about 25 to 90 mole percent and the monomer partial pressure is in the range of from about 75 psia (517 kPa) to about 300 psia (2069 kPa), which are typical conditions in a gas phase polymerization process. In one embodiment, the ethylene partial pressure is about 220 to 240 psi (1517–1653 kPa). In another embodiment, the molar ratio of hexene to ethylene in the reactor is 0.03:1 to 0.08:1.

In a preferred embodiment, the reactor utilized in the present invention and the process of the invention produce greater than 500 lbs of polymer per hour (227 Kg/hr) to about 200,000 lbs/hr (90,900 Kg/hr) or higher of polymer, preferably greater than 1000 lbs/hr (455 Kg/hr), more preferably greater than 10,000 lbs/hr (4540 Kg/hr), even more preferably greater than 25,000 lbs/hr (11,300 Kg/hr), still more preferably greater than 35,000 lbs/hr (15,900 Kg/hr), still even more preferably greater than 50,000 lbs/hr (22,700 Kg/hr) and most preferably greater than 65,000 lbs/hr (29,000 Kg/hr) to greater than 100,000 lbs/hr (45,500 Kg/hr).

Other gas phase processes contemplated by the process of the invention include those described in U.S. Pat. Nos.

5,627,242, 5,665,818 and 5,677,375, and European publications EP-A-0 794 200, EP-A-0 802 202 and EP-B-634 421 all of which are herein fully incorporated by reference.

A slurry polymerization process generally uses pressures in the range of from about 1 to about 50 atmospheres and even greater and temperatures in the range of 0° C. to about 120° C. In a slurry polymerization, a suspension of solid, particulate polymer is formed in a liquid polymerization diluent medium to which ethylene and comonomers and often hydrogen along with catalyst are added. The suspension including diluent is intermittently or continuously removed from the reactor where the volatile components are separated from the polymer and recycled, optionally after a distillation, to the reactor. The liquid diluent employed in the polymerization medium is typically an alkane having from 3 to 7 carbon atoms, preferably a branched alkane. The medium employed should be liquid under the conditions of polymerization and relatively inert. When a propane medium is used the process must be operated above the reaction diluent critical temperature and pressure. Preferably, a hexane or an isobutane medium is employed.

In one embodiment, a preferred polymerization technique of the invention is referred to as a particle form polymerization, or a slurry process where the temperature is kept below the temperature at which the polymer goes into solution. Such technique is well known in the art, and described in for instance U.S. Pat. No. 3,248,179 which is fully incorporated herein by reference. The preferred temperature in the particle form process is within the range of about 185° F. (85° C.) to about 230° F. (110° C.). Two preferred polymerization methods for the slurry process are those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. No. 4,613,484, which is herein fully incorporated by reference.

In another embodiment, the slurry process is carried out continuously in a loop reactor. The catalyst as a solution, a suspension, as an emulsion, as a slurry in isobutane or as a dry free flowing powder is injected regularly to the reactor loop, which is itself filled with circulating slurry of growing polymer particles in a diluent of isobutane containing monomer and comonomer. Hydrogen, optionally, may be added as a molecular weight control. The reactor is maintained at a pressure of about 525 psig to 625 psig (3620 kPa to 4309 kPa) and at a temperature in the range of about 140° F. to about 220° F. (about 60° C. to about 104° C.) depending on the desired polymer density. Reaction heat is removed through the loop wall since much of the reactor is in the form of a double-jacketed pipe. The slurry is allowed to exit the reactor at regular intervals or continuously to a heated low pressure flash vessel, rotary dryer and a nitrogen purge column in sequence for removal of the isobutane diluent and all unreacted monomer and comonomers. The resulting hydrocarbon free powder is then compounded for use in various applications.

In an embodiment, the reactor used in the slurry process of the invention is capable of and the process of the invention is producing greater than 2000 lbs of polymer per hour (907 Kg/hr), more preferably greater than 5000 lbs/hr (2268 Kg/hr), and most preferably greater than 10,000 lbs/hr (4540 Kg/hr). In another embodiment, the slurry reactor used in the process of the invention is producing greater than 15,000 lbs of polymer per hour (6804 Kg/hr), preferably greater than 25,000 lbs/hr (11,340 Kg/hr) to about 100,000 lbs/hr (45,500 Kg/hr).

In another embodiment, in the slurry process of the invention the total reactor pressure is in the range of from 400 psig (2758 kPa) to 800 psig (5516 kPa), preferably 450 psig (3103 kPa) to about 700 psig (4827 kPa), more preferably 500 psig (3448 kPa) to about 650 psig (4482 kPa), most preferably from about 525 psig (3620 kPa) to 625 psig (4309 kPa).

In yet another embodiment, in the slurry process of the invention the concentration of ethylene in the reactor liquid medium is in the range of from about 1 to 10 weight percent, preferably from about 2 to about 7 weight percent, more preferably from about 2.5 to about 6 weight percent, most preferably from about 3 to about 6 weight percent.

A preferred process of the invention is where the process, preferably a slurry or gas phase process is operated in the absence of or essentially free of any scavengers, such as triethylaluminum, trimethylaluminum, tri-isobutylaluminum and tri-n-hexylaluminum and diethyl aluminum chloride, dibutyl zinc and the like. This preferred process is described in PCT publication WO 96/08520 and U.S. Pat. No. 5,712,352, which are herein fully incorporated by reference.

In another preferred embodiment, the one or all of the catalysts are combined with up to 10 weight % of a metal stearate, (preferably a aluminum stearate, more preferably aluminum distearate) based upon the weight of the catalyst system (or its components), any support and the stearate. In an alternate embodiment, a solution of the metal stearate is fed into the reactor. In another embodiment, the metal stearate is mixed with the catalyst and fed into the reactor separately. These agents may be mixed with the catalyst or may be fed into the reactor in a solution or a slurry with or without the catalyst system or its components. More information on using aluminum stearate type additives may be found in U.S. Ser. No. 09/113,261 filed Jul. 10, 1998, which is incorporated by reference herein.

In another preferred embodiment, the supported catalysts combined with the activators are tumbled with 2 weight % of an antistat, such as a methoxylated amine, such as Witco's Kemamine AS-990 from ICI Specialties in Bloomington Del.

Polyolefins, particularly polyethylenes, having a density of 0.89 to 0.97g/cm$^3$ can be produced using this invention. In particular polyethylenes having a density of 0.910 to 0.965, preferably 0.915 to 0.960, preferably 0.920 to 0.955 can be produced. In some embodiments, a density of 0.915 to 0.940 g/cm$^3$ would be preferred, in other embodiments densities of 0.930 to 0.970 g/cm$^3$ are preferred.

The polyolefins then can be made into films, molded articles (including pipes), sheets, wire and cable coating and the like. The films may be formed by any of the conventional techniques known in the art including extrusion, co-extrusion, lamination, blowing and casting. The film may be obtained by the flat film or tubular process which may be followed by orientation in an uniaxial direction or in two mutually perpendicular directions in the plane of the film to the same or different extents. Orientation may be to the same extent in both directions or may be to different extents. Particularly preferred methods to form the polymers into films include extrusion or coextrusion on a blown or cast film line.

The films produced may further contain additives such as slip, antiblock, antioxidants, pigments, fillers, antifog, UV stabilizers, antistats, polymer processing aids, neutralizers, lubricants, surfactants, pigments, dyes and nucleating agents. Preferred additives include silicon dioxide, synthetic silica, titanium dioxide, polydimethylsiloxane, calcium carbonate, metal stearates, calcium stearate, zinc stearate, talc, $BaSO_4$, diatomaceous earth, wax, carbon black, flame retarding additives, low molecular weight resins, hydrocarbon resins, glass beads and the like. The additives may be present in the typically effective amounts well known in the art, such as 0.001 weight % to 10 weight %.

EXAMPLES

In order to provide a better understanding of the present invention including representative advantages thereof, the following examples are offered. The following compounds are well know in the art and are available from many different suppliers:

TIBA is triisobutyl aluminum; MMAO is modified methyl alumoxane; and MAO is methyl alumoxane. Ph is phenyl. Me is methyl.

Example 1

Preparation of 2-(2-Pyridyl)-1,3-propane-bis(2,6-dimethyl)aniline 1.50 gms of 2-(2-pyridyl)-1,3-propaneditosylate (3.15 mmol) was combined with 5.0 mls 2,6-dimethylaniline in a 100 ml Schlenk flask with a stir bar. The flask was heated under nitrogen at 110° C. for 16 hrs, then was allowed to cool to room temperature. ~20 mls diethyl ether was added and swirled until the viscous oil became miscible. The ether solution was extracted three times with water, followed by removal of the solvent in vacuo. The oil was transferred to a short path distillation apparatus and heated under full vacuum. The initial fraction distilling over at 35° C. was discarded. The remaining viscous oil was isolated. 1H NMR THF-$d_8$ 8.64 (1H, m, py), 7.71 (1H, t, py), 7.51 (1H, d, py), 7.21 (1H, m, py), 6.86 (4H, d, meta-aniline), 6.68 (2H, t, para-aniline), 3.80 (2H, br, NH), 3.47 (2H, d, ArN(H)CHH), 3.26 (2H, d, ArN(H)CHH), 2.18 (12H, s, aniline Me), 1.66 (3H, s, MeC($CH_2$)$_2$(py)).

Example 2

Preparation of 2-(2-Pyridyl)-1,3-propane-bis(2, 6dimethyl)aniline Zirconium Dimethyl)

0.234 gms (1.0 mmol) of $ZrCl_4$ was combined with 0.378 gms (1.0 mmol) 2-(2-pyridyl)-1,3-propane-bis(2,6-dimethyl)aniline and ~10 mls toluene in a 100 ml Schlenk flask under a nitrogen atmosphere. The contents were heated to 90–100° C. for 20 hrs with stirring. The solids produced were filtered in the drybox and washed with additional toluene. Yield (0.523 gms, 86%) All of this material (0.86 mmol) was suspended in 15 mls diethyl ether and cooled to ~78° C. under nitrogen in a Schlenk flask. 2.46 mls of 1.4 M MeLi in diethyl ether (3.44 mmol) was added dropwise. The flask was allowed to warm to room temperature over 3 hours. Solvent was removed in vacuo. The product was extracted with toluene followed by filtration to remove solids. 1H NMR C6D6 8.76 (1H, m, pyridyl), 6.53–7.11 (9H, m, pyridyl and aniline), 3.92 (2H, d, CHH), 2.74 (2H, d, CHH), 2.26 (12H, s, aniline Me), 0.96 (3H, s, MeC($CH_2$)$_2$(py)), 0.19 (6H, br, ZrMe). Over time, another resonance appeared at 0.156 ppm, presumably due to methane formation. The product was stable when stored as a solid under nitrogen.

This is a representation of the complex of Example 2:

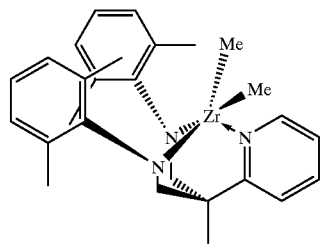

Examples 3 to 12

Ethylene polymerizations using 2-(2-pyridyl)-1,3-propane-bis(2,6-dimethyl)aniline zirconium dimethyl were performed. Polymerizations in a slurry reactor were conducted as follows. After an appropriate bake-out period and subsequent cool-down under nitrogen, 500 cc's of hexanes were charged to a 1 liter autoclave reactor. 1-Hexene, if any, and scavenger, if any, were added to the reactor prior to heating. The reactor contents were heated to the desired temperature. A mixture of the catalyst and cocatalyst were prepared in the glovebox in an airtight syringe, removed to the reactor and injected into the reactor once it had reached reaction temperature. Ethylene immediately filled the system to obtain a total pressure of 150 psig (1.03 MPa) and was fed on demand thereafter. Polymerizations were conducted for 30 minutes. BBF indicates butyl branching frequency (per 1000 C).

TABLE 1

| Example | umol Zr | activator | Ratio | scavenger | ratio | temp | hexene | yield (gms) | BBF (IR) |
|---|---|---|---|---|---|---|---|---|---|
| 3 | 2 | MAO + MMAO | 1000 | none | | 85 | 0 | 0 | |
| 4 | 10 | B(C6F5)3 | 1.2 | TIBA | 50 | 85 | 0 | 0 | |
| 5 | 5 | B(C6F5)3 | 7.5 | MMAO | 350 | 85 | 0 | 2 | |
| 6 | 5 | Ph3C B(C6F5)4 | 1.2 | TIBA | 50 | 65 | 0 | 0.8 | |
| 7 | 5 | Ph3C B(C6F5)4 | 1.2 | TIBA | 50 | 85 | 0 | 4.5 | |
| 8 | 5 | Ph3C B(C6F5)4 | 1.2 | TIBA | 50 | 95 | 0 | 0.1 | |
| 9 | 5 | Ph3C B(C6F5)4 | 1.2 | TIBA | 50 | 85 | 20 | 3.2 | 22.5 |
| 10 | 5 | PhN(Me)2H B(C6F5)4 | 1.2 | TIBA | 50 | 65 | 0 | 0 | |
| 11 | 5 | PhN(Me)2H B(C6F5)4 | 1.2 | TIBA | 50 | 85 | 0 | 4.5 | |
| 12 | 5 | PhN(Me)2H B(C6F5)4 | 1.2 | TIBA | 50 | 85 | 20 | 5 | 19.9 |

Temperature in Table 1 is in ° C.

Example 13 to 18

Hexene polymerizations using 2-(2-pyridyl)-1,3-propane-bis(2,6-dimethyl)aniline zirconium dimethyl). In a glovebox, five mls 1-hexene, stored over Na/K alloy under nitrogen, were purified by passing through an activated basic alumina column directly into 20 ml scintillation vials, each equipped with a stir bar. To each was added 0.25 ml of a 4.2 M stock solution of 2-(2-pyridyl)-1,3-propane-bis(2,6-dimethyl)aniline zirconium dimethyl in toluene. Stock solutions of the appropriate activator were prepared as follows and added to the appropriate vial: 1.15 ml of 0.865M TIBA/heptane solution to example 13; 0.31 ml of a 3.5M MAO/toluene solution for example 14, 0.57 ml of a 1.73M MMAO/heptane solution for example 15, and 1.0 ml of 1.2 mM $B(C_6F_5)_3$, or $PhN(Me)_2H\ B(C_6F_5)_4$, or $Ph_3C\ B(C_6F_5)_4$ toluene solution for 16–18, respectively. The mixtures were capped and allowed to stir overnight. Observations were noted. Workup of 17 and 18 constituted stripped off the remaining 1-hexene. SEC analysis was conducted in THF using a polystyrene standard.

TABLE 2

| Example | umols Zr | Activator | ratio | comments | Mw (SEC) | PDI (SEC) |
|---|---|---|---|---|---|---|
| 13 | 1 | TIBA | 1000 | no apparent reaction | | |
| 14 | 1 | MAO | 1000 | no apparent reaction | | |
| 15 | 1 | MMAO | 1000 | no apparent reaction | | |
| 16 | 1 | B(C6F5)3 | 1.2 | no apparent reaction | | |
| 17 | 1 | PhN(Me)2H B(C6F5)4 | 1.2 | solution viscous after overnight stirring | 544,000 | 2.17 |
| 18 | 1 | Ph3C (C6F5)4 | 1.2 | solution most viscous after overnight stirring | 691,000 | 1.99 |

All documents described herein are incorporated by reference herein, including any priority documents and/or testing procedures. As is apparent form the foregoing general description and the specific embodiments, while forms of the invention have been illustrated and described, various modifications can be made without departing from the spirit and scope of the invention. Accordingly it is not intended that the invention be limited thereby.

I claim:

1. A polymerization process comprising combining in a polymerization reactor one or more olefins with an activator and a catalyst compound, the catalyst compound represented by the following formula:

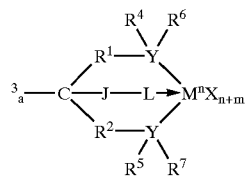

wherein

M is a Group 3, 4 or 5 transition metal or a lanthanide or actinide group metal;

each X is independently an anionic leaving group;

n is the oxidation state of M;

a is 1;

m is the formal charge of the YZL ligand;

Y is a Group 15 element;

Z is a Group 15 element;

J is selected from a $C_1$ to $C_{20}$ hydrocarbon groups;

L is a group comprising a Group 15 or 16 element, wherein J may form a ring structure with L;

$R^1$ and $R^2$ are independently selected from a $C_1$ to $C_{20}$ hydrocarbon groups;

$R^3$ is hydrogen, a hydrocarbyl group;

$R^6$ and $R^7$ are independently absent or selected from hydrogen, halogen, a hydrocarbyl group; and wherein $R^4$ and $R^5$ are independently a group represented by the following formula:

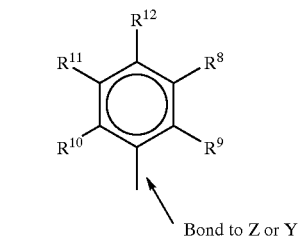

Bond to Z or Y wherein $R^8$, $R^9$, $R^{10}$ and $R^{11}$ are each independently selected from hydrogen, a $C_1$ to $C_{40}$ alkyl group; and $R^{12}$ is hydrogen; wherein any two R groups may form a cyclic group;

and wherein the catalyst compound, activator, or the catalyst compound and activator are supported.

2. The process of claim 1, wherein the activator is selected from alumoxanes, modified alumoxanes, non-coordinating anions, non-coordinating Group 13 metal and metalloid anions, boranes and borates and mixtures thereof.

3. The process of claim 1, wherein the activator is selected from:

trimethylammonium tetraphenylborate; triethylammonium tetraphenylborate, tripropylammonium tetraphenylborate; tri(n-butyl)ammonium tetraphenylborate, tri(t-butyl)ammonium tetraphenylborate; N,N- dimethylanilinium tetraphenylborate, N,N-diethylanilinium tetraphenylborate; N,N-dimethyl-(2,4,6-trimethylanilinium)tetraphenylborate; trimethylammonium tetrakis(pentafluorophenyl)borate; triethylammonium tetrakis(pentafluorophenyl)borate; tripropylammonium tetrakis(pentafluorophenyl)borate; tri(n-butyl)ammonium tetrakis(pentafluorophenyl)borate; tri(sec-butyl)ammonium tetrakis(pentafluorophenyl)borate; N,N-dimethylanilinium tetrakis(pentafluorophenyl)borate; N,N-diethylanilinium tetrakis(pentafluorophenyl)borate; N,N-dimethyl-(2,4,6-trimethylanilinium)tetrakis(pentafluorophenyl)borate, trimethylammonium tetrakis-(2,3,4,6-tetrafluorophenylborate; triethylammonium tetrakis-(2,3,4,6-tetrafluorophenyl)borate; tripropylammonium tetrakis-(2,3,4,6-tetrafluorophenyl)borate; tri(n-butyl)ammonium tetrakis-(2,3,4,6-tetrafluoro-phenyl)borate; dimethyl(t-butyl)ammonium tetrakis-(2,3,4,6-tetrafluorophenyl)borate; N,N-dimethylanilinium tetrakis-(2,3,4,6-tetrafluorophenyl)borate; N,N-diethylanilinium tetrakis-(2,3,4,6-tetrafluoro-phenyl)borate; N,N-dimethyl-(2,4,6-trimethylanilinium)tetrakis-(2,3,4,6-tetrafluorophenyl)borate; di-(i-propyl) ammonium tetrakis(pentafluorophenyl)borate; dicyclohexylammonium tetrakis (pentafluorophenyl)borate; triphenylphosphonium tetrakis(pentafluorophenyl)borate; tri(o-tolyl)phosphonium tetrakis(pentafluorophenyl)borate; tri(2,6-dimethylphenyl) phosphonium tetrakis (pentafluorophenyl)borate, and mixtures thereof.

4. The process of claim 1, wherein the one or more olefins are selected from ethylene, propylene, 1-butene, 1-pentene, 4-methyl-1-pentene, 1-hexene, 1-octene, 1-decene, 3-methyl-1-pentene, norbornene, norbornadiene, 3,5,5-trimethyl-1-hexene and mixtures thereof.

5. The process of claim 1, wherein the one or more olefins comprises from two to thirty carbon atoms.

6. The process of claim 1, wherein the polymerization reactor is a gas phase polymerization reactor.

7. The process of claim 1, wherein the polymerization reactor is a slurry phase polymerization reactor.

8. The process of claim 1, wherein the support is selected from silica, fumed silica, alumina, silica-alumina, magnesia, titania, zirconia, magnesium chloride, montmorillonite, phyllosilicate, zeolites, talc, clays, porous acrylic polymers, nanocomposites, aerogels, spherulites, polymeric beads, and mixtures thereof.

9. The process of claim 1, wherein M is a Group 4, 5 or 6 transition metal.

10. The process of claim 1, wherein each X is independently selected from hydrogen, a hydrocarbyl group, and a halogen.

11. The process of claim 1, wherein L is nitrogen.

12. The process of claim 1, wherein J is a $C_6$ to $C_{20}$ aryl group.

13. The process of claim 1, wherein Y is nitrogen.

14. The process of claim 1, wherein Z is nitrogen.

15. The process of claim 1, wherein $R^9$ and $R^{10}$ are methyl groups, and $R^8$, $R^{11}$ and $R^{12}$ are hydrogen.

16. The process of claim 1, wherein $R^1$ and $R^2$ are independently a $C_1$ to $C_{20}$ alkylene, $C_6$ to $C_{20}$ arylene or $C_7$ to $C_{20}$ arylalkylene group.

17. The process of claim 1, wherein J and L form a pyridyl group.

* * * * *